United States Patent [19]

Girard

[11] 4,182,041

[45] Jan. 8, 1980

[54] DENTAL PROPHYLACTIC RIGHT ANGLE HAND PIECE

[75] Inventor: Howard W. Girard, Dearborn, Mich.

[73] Assignee: Girard, Inc., Lisle, Ill.

[21] Appl. No.: 936,414

[22] Filed: Aug. 24, 1978

Related U.S. Application Data

[63] Continuation of Ser. No. 753,035, Dec. 22, 1976, abandoned.

[51] Int. Cl.² .............................................. A61C 3/06
[52] U.S. Cl. .................................... 433/115; 433/125
[58] Field of Search ............................... 32/59, 27, 58; 128/62 A

[56] References Cited

U.S. PATENT DOCUMENTS

| | | | |
|---|---|---|---|
| 689,596 | 12/1901 | Platt | 32/59 |
| 1,179,216 | 4/1916 | Ragatz | 32/59 |
| 1,499,345 | 7/1924 | Chott | 32/59 |
| 1,499,346 | 7/1924 | Chott | 32/59 |
| 1,673,913 | 6/1928 | Jurgensen | 32/59 |
| 1,720,017 | 7/1929 | Touchstone | 32/59 |
| 3,389,468 | 6/1968 | Lewis et al. | 128/62 A |
| 3,407,502 | 10/1968 | Richmond | 32/59 |
| 3,740,853 | 6/1973 | Brahler | 32/59 |
| 3,757,419 | 9/1973 | Hopkins | 32/59 |
| 3,758,948 | 9/1973 | Bareth | 32/27 |

FOREIGN PATENT DOCUMENTS 2302630 7/1974 Fed. Rep. of Germany ............. 32/59

*Primary Examiner*—Russell R. Kinsey
*Assistant Examiner*—John J. Wilson
*Attorney, Agent, or Firm*—Trexler, Wolters, Bushnell & Fosse, Ltd.

[57] ABSTRACT

The dental prophylactic right angle hand piece of the knob type includes conventional driving and driven members, with the driven member including an integral collar and an integral serrated knob to which the dental application or cup is releasably secured for preventing the cup from slipping under pressure. The collar forms an effective seal between the head of the hand piece and the cup to prevent bacteria from entering the interior of the hand piece. With such a construction the hand piece can be operated forwardly or backwardly without the cup slipping or falling out of the hand piece.

1 Claim, 2 Drawing Figures

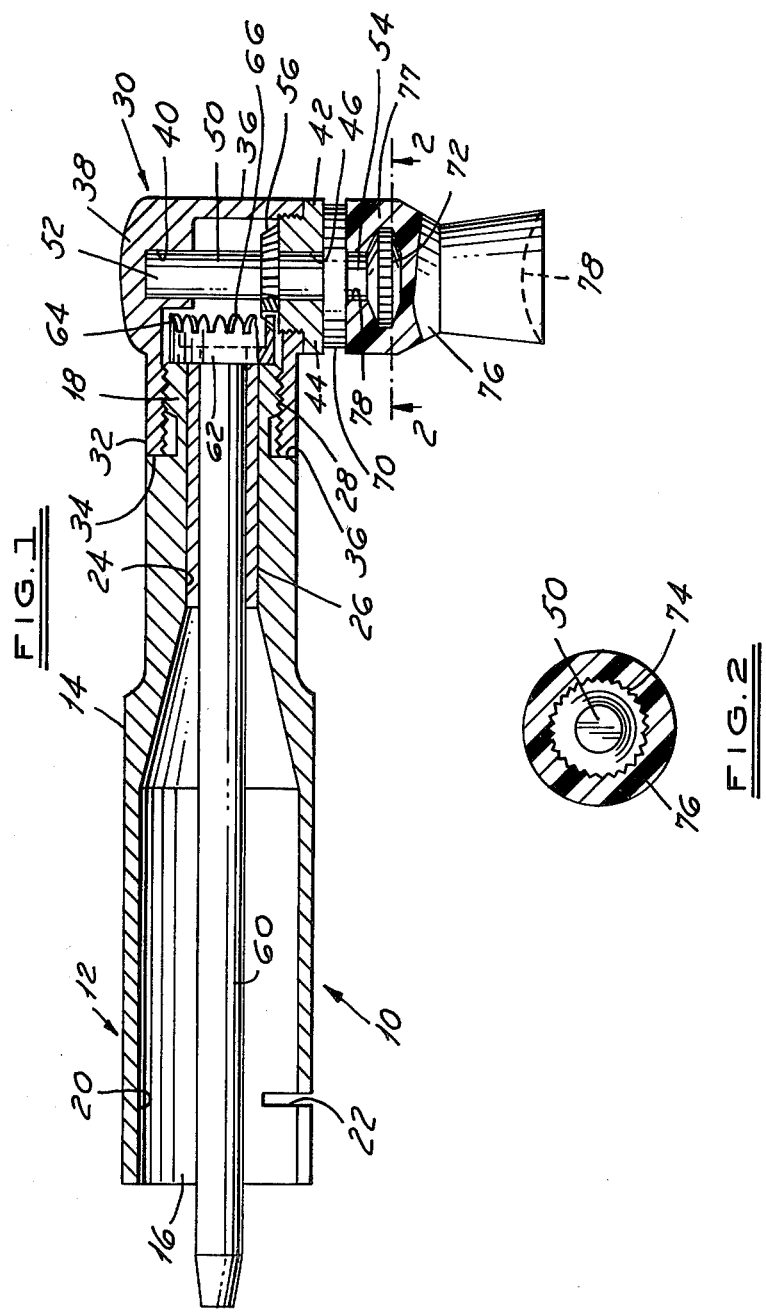

DENTAL PROPHYLACTIC RIGHT ANGLE HAND PIECE

This is a continuation of application Ser. No. 753,035, filed Dec. 22, 1976, and abandoned Sept. 11, 1978.

BACKGROUND OF THE INVENTION

1. Field of the Invention

This invention is for use in the field of dental health where dentists or dental hygienists treat patients by cleaning and polishing teeth and/or by massaging gums.

2. Description of the Prior Art

The mechanical prophylactic angle hand pieces of the knob type are used extensively. The knob of the hand piece is smooth and the rubber cup inserted over the knob slips or stops under pressure. In other cases the rubber cup or dental applicator falls out of the hand piece.

This invention is an improvement on a hand piece of the type disclosed in the Graham U.S. Pat. No. 3,727,313 of Apr. 17, 1973 and in the patents cited therein. Other prior art patents lcoated during a novelty search include the Burlow U.S. Pat. No. 1,314,125 of Aug. 26, 1919; Stempel U.S. Pat. No. 1,417,584 of May 30, 1922; Blair U.S. Pat. No. 2,135,933 of Nov. 8, 1938; and the Kean et al U.S. Pat. No. 3,142,138 of July 28, 1964.

In the past the rubber cups have in certain cases been positively secured to the driven members by screws. This requires time to complete and is an inconvenience to the dentist.

SUMMARY OF THE INVENTION

The present invention is primarily directed to the driven member of a conventional dental prophylactic right angle hand piece where an integral knob is provided which has an annular row of sharp serrations around the entire periphery thereof so that when the rubber cup is slipped over the serrated knob, the serrations or sharp teeth will bite into or positively grip the cup thus preventing the cup from slipping. Thus the sharp serrations on the perimeter of the knob causes a locking action into the rubber cup, eliminating any possibility of slippage or the cup falling out of the hand piece.

The driven member of the present invention includes an integral serrated knob and an integral collar which helps to eliminate the transfer of bacteria or infection into the interior parts of the hand piece by providing a positive seal. The driven member of the present invention may be installed in any of the new commercially available hand pieces made from metal.

Thus it is a feature of the present invention to provide a right angle dental hand piece having a serrated tool holding knob for releasable securement thereon of the elastic rubber base of a cleaning and polishing cup or other element or tool, and which knob, as a result of the serrated teeth, more positively hold the cup or base on the knob against rotation relative thereto during a dental treatment than the devices shown in the aforementioned prior art patents.

DESCRIPTION OF THE DRAWINGS

FIG. 1 is a cross-sectional view through a dental hand piece in which a cleaning and polishing cup, or dental tool is releasably held on the driven member of the hand piece; and FIG. 2 is a cross-sectional view taken on the line 2—2 of FIG. 1 and showing the annular row of pointed gear teeth formed on the driven member.

DESCRIPTION OF A PREFERRED EMBODIMENT

The dental prophylactic right angle hand piece is designated by the numeral 10 and includes a body 12 that comprises an elongated generally cylindrical tubular shank 14 having an inner end 16 and an outer end 18 and a bore 20 extending axially therethrough. The bore 20 has inner and outer axially directed ends respectively at the inner and outer ends 16, 18 of the shank 14. The inner end 16 of shank 18 has a slot 22 for connecting the hand piece 10 with a coupling or the like that, in turn, is connected to a power source, not shown.

The bore 20 is reduced in diameter near the outer end thereof where the reduced bore 24 receives a bushing 26. The outer end of the shank 14 is externally threaded as indicated by the numeral 28. The outer end of bushing 26 is flush with the threaded outer end of the shank 14.

A hollow head 30 is provided with an internally threaded sleeve 32 which threadedly receives the threaded outer end 28 of the shank. The sleeve 32 has an end face 34 which abuts an annular shoulder 36 provided on the shank 14.

The head 30 has side walls 36, an integral top wall 38 having a recess, cavity or bearing area 40 therein and a bottom wall 42. The lower ends of the side walls 36 is internally threaded and receives an external threaded closure or plug 44 which forms the bottom wall 42. The plug 44 has a centrally located bearing opening 46 therein.

An elongated driven generally cylindrical member 50 is rotatably mounted in the head 30, with the upper end portion 52 received in the bearing 40 provided in the top wall 38 and the lower end portion 54 thereof extending through the bearing opening 46 in the plug 44 and terminating exteriorly of the plug 44. The driven member 50 is rotated about an axis perpendicular to the longitudinal axis of the shank 14 and bore 20, 24.

The novel driven member 50 is provided with driven means 56 integral therewith in the form of an annular row of gear teeth coaxial with the axis of the driven member 50.

An elongated driving spindle 60 is rotatably supported within the bore 20 of the shank 14 and is coaxial therewith. The spindle 60 has a terminal end portion 62 extending beyond the outer end of the reduced bore 24 which is provided with driving means 64 integral with the spindle 60. The driving means 64 comprises an annular row of gear teeth 66 coaxial with the spindle. The gear teeth 66 have terminal outer end portions around the outer end of the spindle 60 which are positioned between the annular row of gear teeth on the driven member 50. With such a construction the gear teeth of the spindle 60 and of the driven member 50 are in intermeshing relation.

The novel driven member 50 further includes an integral collar 70 which abuts the end plug 44 and a serrated knob 72 which is spaced from collar 70 and forms the terminal end of the driven member 50.

The serrated knob 72 is in the form of an annular row of pointed gear teeth 74 coaxial with the driven member 50 and which are sharp and are formed at an acute angle as noted in FIG. 2. The sides or flanks of the teeth 74 are straight and taper towards the crests of the teeth, each of which crests is pointed. The pointed teeth 74 form cutting edges at the crests thereof which cut into the resilient dental tool to be secured thereto.

A dental applicator, tool or rubber cup or tip 76 is releasably attached to the serrated knob 72. The cup 76 is elastic and has a base 77 provided with a socket or recess 78 which stretches and fits over the serrated pointed and cutting teeth 74 and encloses the serrated knob 72 as shown in FIG. 1.

The sharp teeth 74 provided on the knob 72 causes a positive locking and biting action into the resilient or elastic cup 76, thus, eliminating any possibility of slippage or stoppage or of the cup 76 falling off the hand piece 10.

The elastic rubber cup 76 is conventional and is shown in the prior art patents. The cup 76 has the recess 78 in its base end for receiving the serrated knob 72 when the base end is stretched over the knob 72. The axially outwardly opening recess 78 holds cleaning and polishing powder when is use, and applies the powder to the teeth when the member 50 is rotated and the open end of the cup is pressed against the teeth.

The cup 76 is not a part of the hand piece 10, but is representative of one form of dental tool adapted to be supported on the driven member 50 of the hand piece 10 when the latter is in use. Other tools having bristles providing a brush instead of a cup, or having a structure other than a cup or brush may be releasably secured on the serrated knob 72 in the same manner as described herein.

I claim:

1. A dental prophylactic right angle hand piece comprising: an elongated tubular shank having an inner end and an outer end, and a bore extending axially therethrough, said bore having inner and outer axially directed ends respectively at said inner and outer ends of said shank, said outer end of said shank being threaded, a hollow head provided with an internally threaded sleeve for threadedly securing said head to the threaded outer end of said shank, said head having side walls and a pair of opposite end walls, an elongated driven member rotatably supported within said head about an axis perpendicular to the axis of said shank, said driven member including a portion extending through one of the end walls of said head, an elongated driving spindle rotatably supported within the bore of said shank coaxial therewith and having a terminal end portion extending beyond the outer end of said bore, said spindle and said driven member including driving means integral with said spindle and driven means integral with said driven member in driving relation to each other, said driven means comprising an annular row of gear teeth on said driven member coaxial with the axis of said driven member, said driving means comprising an annular row of gear teeth on said spindle coaxial therewith having terminal outer end portions around the outer end of said spindle positioned between the annular row of gear teeth on said driven member, said terminal outer end portions being in intermeshing driving relation with the teeth on said driven member, said one end wall being in the form of an externally threaded plug which is threadedly carried by the side walls of said head, said plug having an opening therein through which said driven member extends, said extending portion of said driven member including an integral collar sealably abutting said plug to provide a barrier to the entry of bacteria into the internal parts of said hand piece and an integral serrated knob at the terminal end of said driven member which is spaced from said collar, said serrated knob being arranged in the form of an annular row of gear teeth which is coaxial with the axis of said driven member, and a disposable resilient dental applicator having a generally flat surface removably abutting said collar to form a seal therebetween, said applicator having a blind hole socket adjacent said flat surface, said socket being provided with an axis which coincides with the axis of said driven member, said socket of said dental applicator being stretched to fit over and to enclose said serrated knob whereby the teeth of said knob cut into said resilient dental applicator thus forming a positive lock therebetween and eliminating slippage of said applicator on said serrated knob, the seal formed between said collar and said applicator forming a barrier to the entry of bacteria into the socket of said dental applicator and the associated serrated knob.

* * * * *